(12) United States Patent  
Karthikeyan et al.

(10) Patent No.: US 10,216,910 B2
(45) Date of Patent: Feb. 26, 2019

(54) SIMULATED CARBON AND PROTON NMR CHEMICAL SHIFTS BASED BINARY FINGERPRINTS FOR VIRTUAL SCREENING

(71) Applicant: COUNCIL OF SCIENTIFIC & INDUSTRIAL RESEARCH, New Delhi (IN)

(72) Inventors: Muthukumarasamy Karthikeyan, Maharashtra (IN); Renu Vyas, Maharashtra (IN); Pattuparambil Ramanpillai Rajamohanan, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 486 days.

(21) Appl. No.: 14/901,151

(22) PCT Filed: Jun. 25, 2014

(86) PCT No.: PCT/IB2014/062585
§ 371 (c)(1),
(2) Date: Dec. 28, 2015

(87) PCT Pub. No.: WO2014/207670
PCT Pub. Date: Dec. 31, 2014

(65) Prior Publication Data
US 2016/0140326 A1  May 19, 2016

(30) Foreign Application Priority Data
Jun. 25, 2013  (IN) .......................... 1874/DEL/2013

(51) Int. Cl.
*C40B 30/02* (2006.01)
*G06F 19/00* (2018.01)

(52) U.S. Cl.
CPC ............ *G06F 19/703* (2013.01); *C40B 30/02* (2013.01); *G06F 19/705* (2013.01)

(58) Field of Classification Search
CPC ..................................................... G06F 19/703
(Continued)

(56) References Cited

U.S. PATENT DOCUMENTS 7,181,348 B2 * 2/2007 Wishart ............ G01R 33/4625
436/173
2003/0229456 A1 * 12/2003 Beger .................. G06F 19/704
702/27

(Continued)

FOREIGN PATENT DOCUMENTS

JP        06034730 A      2/1994
WO    2008-066672 A2    6/2008

OTHER PUBLICATIONS

Kooistra et al. (Electron Density Fingerprints (EDprints): Virtual Screening Using Assembled Information of Electron Density, J. Chem. Inf. Model. 2010, 50, 1772-1780).*

(Continued)

*Primary Examiner* — Kamini S Shah
*Assistant Examiner* — Iftekhar A Khan
(74) *Attorney, Agent, or Firm* — Baker & Hostetler LLP

(57) ABSTRACT

The invention discloses a method to generate and analyze NMR chemical shift based binary fingerprints for virtual high throughput screening in drug discovery. Further, the invention provides a method to analyze NMR chemical shifts based binary fingerprints that has implications for encoding several properties of a molecule besides the basic framework or scaffold and determine its propensity towards a particular bioactivity class.

13 Claims, 20 Drawing Sheets

(58) Field of Classification Search
USPC .......................................................... 703/1
See application file for complete search history.

(56) References Cited

U.S. PATENT DOCUMENTS

| | | | |
|---|---|---|---|
| 2004/0014168 A1* | 1/2004 | Schreiber | C07D 311/78 435/68.1 |
| 2007/0015813 A1* | 1/2007 | Carter | A61K 31/404 514/414 |
| 2007/0043518 A1* | 2/2007 | Nicholson | G06F 19/703 702/23 |
| 2007/0156342 A1* | 7/2007 | Frimurer | G06F 19/16 702/19 |
| 2010/0010946 A1* | 1/2010 | De Winter | G06F 19/706 706/13 |
| 2010/0144587 A1* | 6/2010 | Piccariello | A61K 31/19 514/6.9 |
| 2016/0015828 A1* | 1/2016 | Torgov | C07K 16/3023 424/181.1 |

OTHER PUBLICATIONS

Kapetanovic et al. (Computer-Aided Drug Discovery and Development (CADDD): in silico-chemico-biological approach, Chem Biol Interact. Jan. 30, 2008; 171(2): 165-176).*

Butkiewicz et al. (Benchmarking Ligand-Based Virtual High-Throughput Screening with the PubChem Database, Molecules 2013, 18, 735-756).*

Ma et al. (In-silico approaches to multi-target drug discovery computer aided multi-target drug design, multi-target virtual screening, Pharmaceutical Research • Mar. 2010, pp. 739-749).*

Bender et al. (Similarity Searching of Chemical Databases Using Atom Environment Descriptors (MOLPRINT 2D): Evaluation of Performance, J. Chem. Inf. Comput. Sci. 2004, 44, 1708-1718).*

Ekins et al. (In silico pharmacology for drug discovery: methods for virtual ligand screening and profiling, British Journal of Pharmacology (2007) 152, 9-20).*

Kapetanovic et al. (Computer-Aided Drug Discovery and Development (CADDD): in silico-chemico-biological approach, Chem Biol Interact. Jan. 30, 2008; 171(2): 165-176) (Year: 2008).*

Butkiewicz et al. (Benchmarking Ligand-Based Virtual High-Throughput Screening with the PubChem Database, Molecules 2013, 18, 735-756) (Year: 2013).*

Ma et al. (In-silico approaches to multi-target drug discovery computer aided multi-target drug design, multi-target virtual screening, Pharmaceutical Research, May 2010, pp. 739-749) (Year: 2010).*

Bender et al. (Similarity Searching of Chemical Databases Using Atom Environment Descriptors (MOLPRINT 2D): Evaluation of Performance, J. Chem. Inf. Comput. Sci. 2004, 44, 1708-1718) (Year: 2004).*

Kooistra et al., "Electron Density Fingerprints (EDprints): Virtual Screening Using Assembled Information of Electron Density", Journal of Chemical Information and Modeling, vol. 50, No. 10, Oct. 25, 2010, pp. 1772-1780.

D. S. Egolf et al., "Simulation of Carbon-13 Nuclear Magnetic Resonance Spectra of Methyl-Substituted Norbornan-2-ols", Anal. Chem., 1988, vol. 60, pp. 2700-2706.

A. J. Kooistra et al., "Electron Density Fingerprints (EDprints): Virtual Screening Using Assembled Information of Electron Density", J. Chem Inf. Model, 2010, vol. 50, pp. 1772-1780.

C. Fernandez et al., "News Approaches for NMR Screening in Drug Discovery", Drug Discovery Today: Technologies, 2004, vol. 1, pp. 277-283.

* cited by examiner

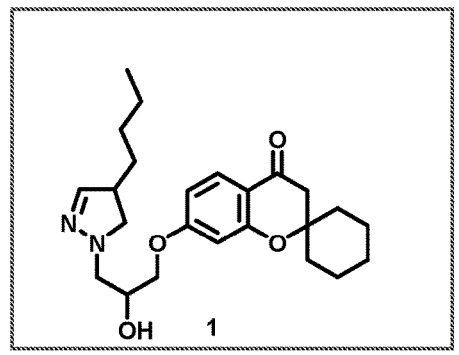
7-(3-(4-butyl-4,5-dihydro-1H-pyrazol-1-yl)-2-hydroxypropoxy)spiro[chromane-2,1'-cyclohexan]-4-one
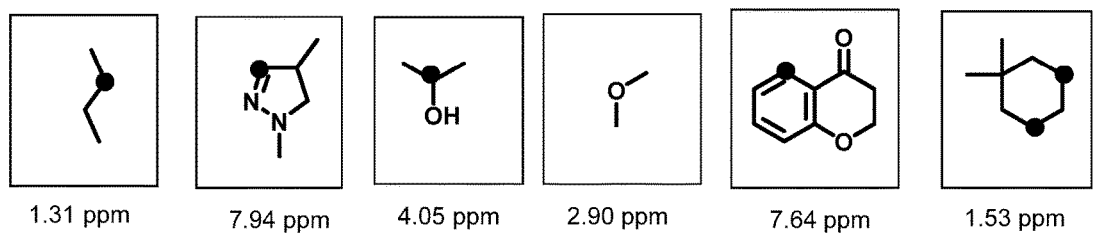
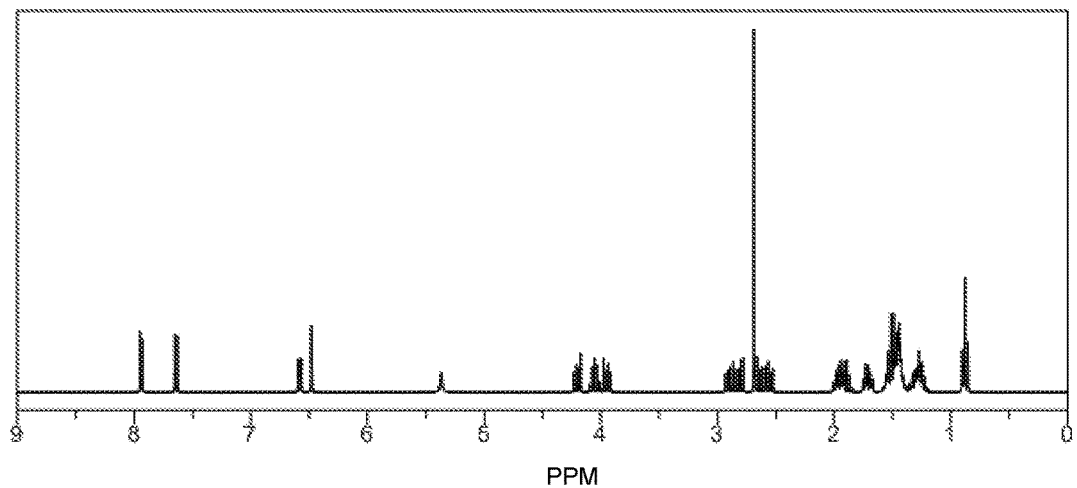
Fig 1(a)

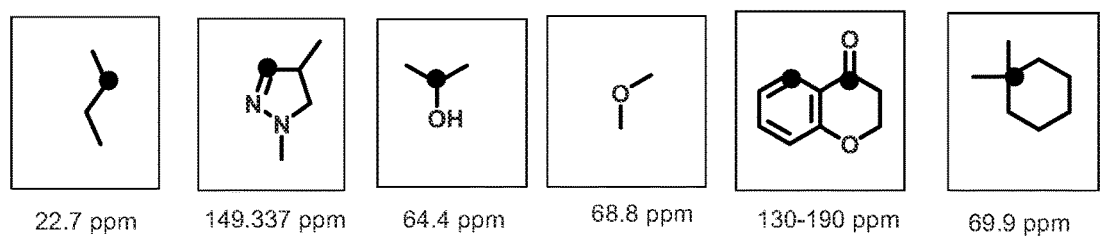
22.7 ppm  149.337 ppm  64.4 ppm  68.8 ppm  130-190 ppm  69.9 ppm
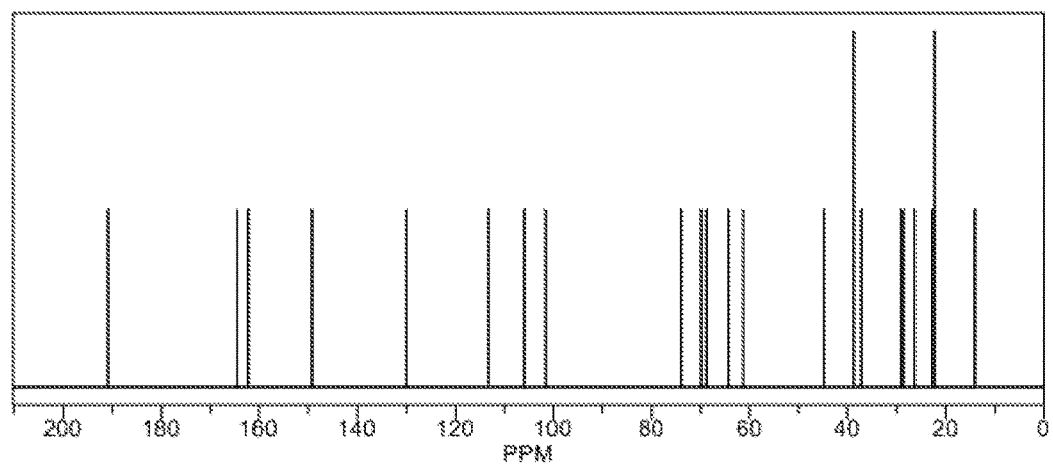
Fig 1(b)

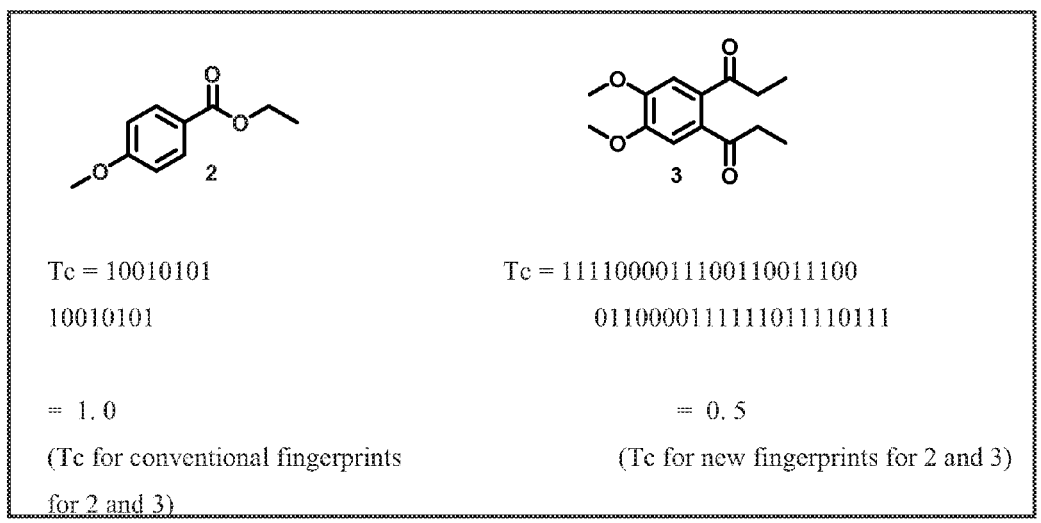
Figure 2c
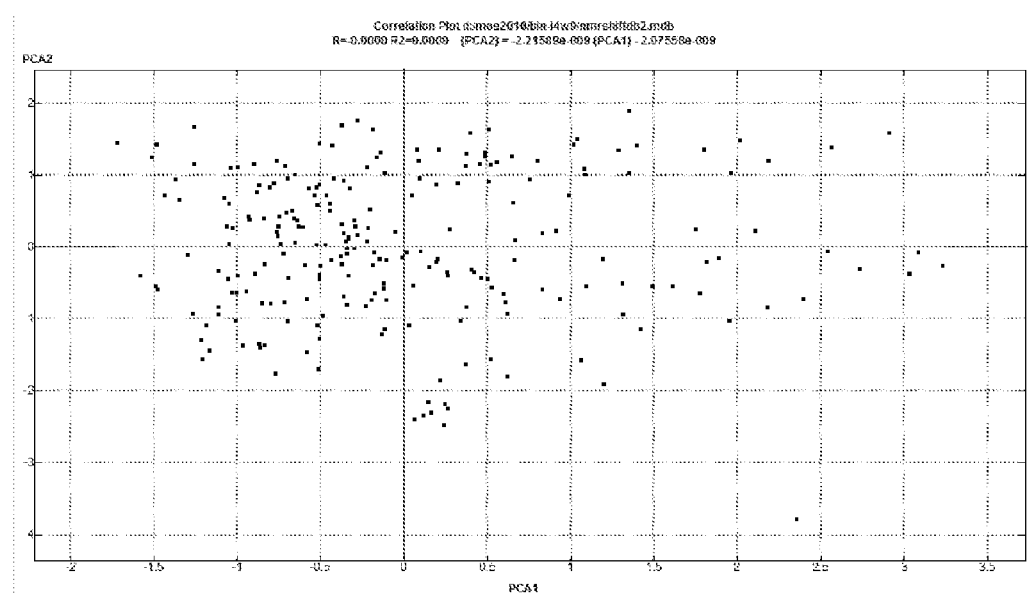
Figure 3 : 2D PCA plot of the nmr dataset

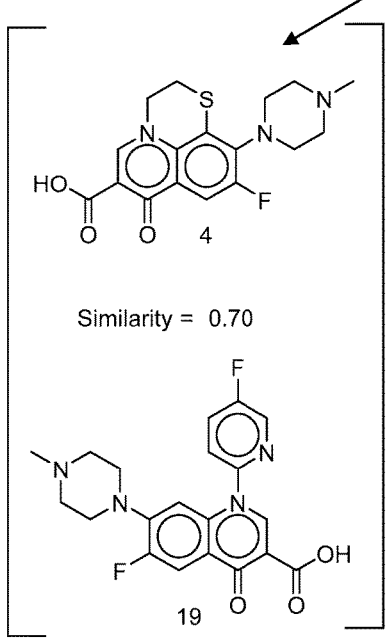
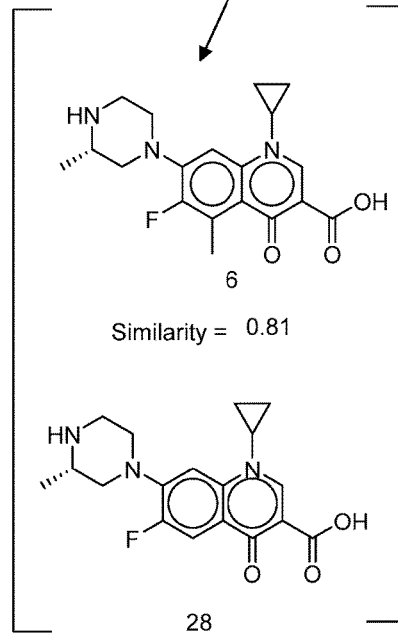
Figure 12a:

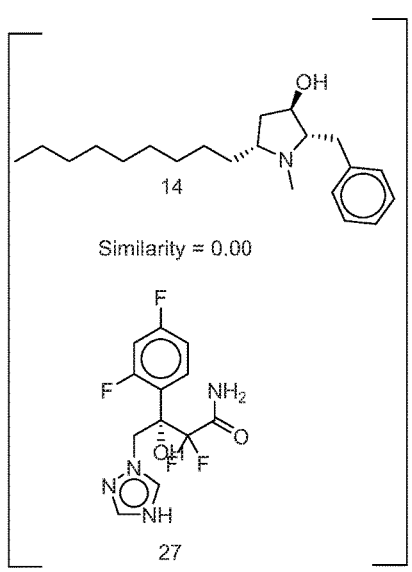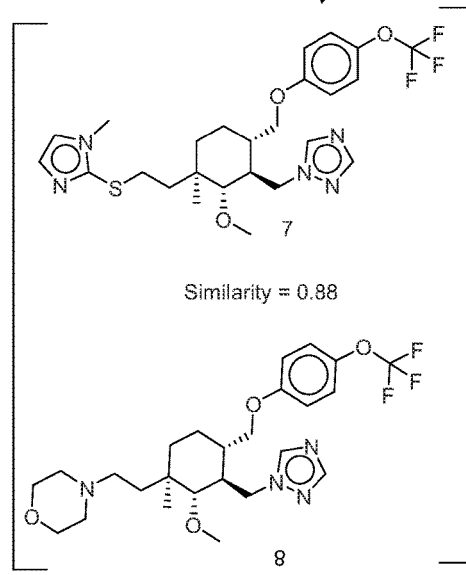
Figure 12b

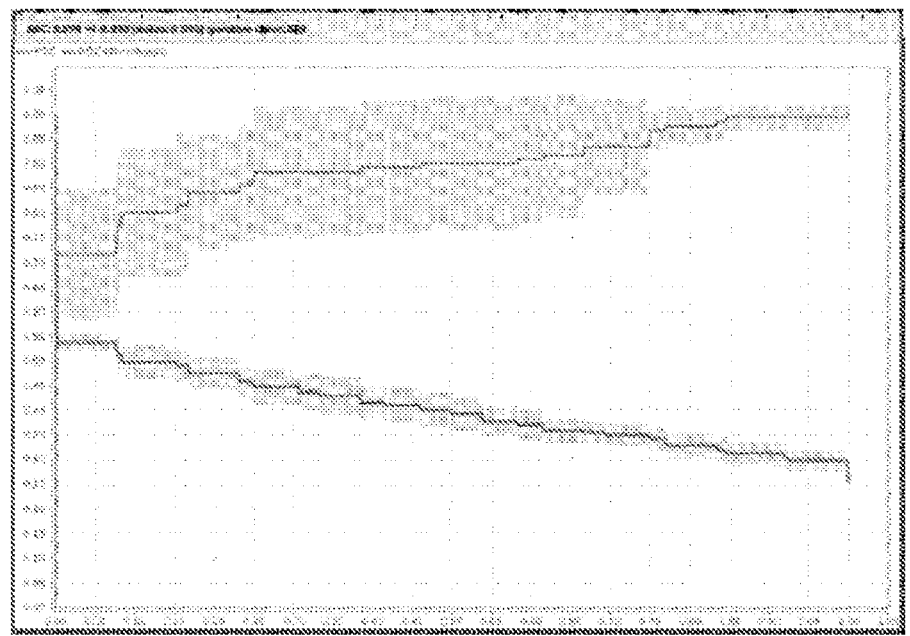
Figure 14: AUC curve
| C-CH3 | RNH2 | CH3-CH=CH2 | SR |
|---|---|---|---|
| 0.9-1.7 ppm | 1.4 ppm | 1.7 ppm | 2.1 ppm |
| ROH | SOR | CH3-O | RCOO-C-H |
| 2-5 ppm | 2.6 ppm | 3-4 ppm | 3.7-4.1 ppm |
| OCO-CF3 | -NO2 | phenol-OH | benzene |
| 4.0 ppm | 4.1 ppm | 4-7 ppm | 7.1-8 ppm |
| RCHO | RCOOH | C=C-OH | |
| 9-10 ppm | 10-12 ppm | 15-17 ppm | |
Figure 15: Typical proton chemical shift $\delta$ of commonly occurring functional groups

Figure 16: Typical carbon chemical shift δ of commonly occurring functional groups

```
Results :
    AUC: 0. 895 +/- 0. 090 (mikro: 0. 895) (positive class: AB)
    PerformanceVector:
    accuracy: 83. 70% +/- 7.13% (mikro: 83. 74%)
    ConfusionMatrix:
    True:   AF    AB
    AF:     114   28
    AB:     12    92
    precision: 89. 44% +/- 9.08% (mikro: 88. 46%) (positive class: AB)
    ConfusionMatrix:
    True:   AF    AB
    AF:     114   28
    AB:     12    92
    recall: 76. 67% +/- 12.25% (mikro: 76. 67%) (positive class: AB)
    ConfusionMatrix:
    True:   AF    AB
    AF:     114   28
    AB:     12    92
    AUC (optimistic): 0. 895 +/- 0. 090 (mikro: 0. 895) (positive class: AB)
    AUC: 0. 895 +/- 0. 090 (mikro: 0. 895) (positive class: AB)
    AUC (pessimistic): 0. 895 +/- 0. 090 (mikro: 0. 895) (positive class: AB)
```

Figure 17A: Results for antibacterial dataset using SVM classifier in Rapid miner

|           | true AF | true AB | class precision |
|-----------|---------|---------|-----------------|
| pred. AF  | 114     | 28      | 80. 28%         |
| pred. AB  | 12      | 92      | 88. 46%         |
| class recall | 90. 48% | 76. 67% |             |

Figure 17B: Results for antibacterial dataset using SVM classifier in Rapid miner

SIMULATED CARBON AND PROTON NMR CHEMICAL SHIFTS BASED BINARY FINGERPRINTS FOR VIRTUAL SCREENING

CROSS REFERENCE TO RELATED APPLICATIONS

This application is a National Stage of International Application No. PCT/IB2014/062585, filed on Jun. 25, 2014, which claims priority to Indian patent application no. 1874/DEL/2013, filed on Jun. 25, 2013, the disclosures of which are incorporated by reference in their entirety.

FIELD OF THE INVENTION

This invention relates to a method to identify/analyze NMR (Nuclear Magnetic Resonance) chemical shifts based binary fingerprints for virtual high throughput screening in drug discovery. More particularly, the invention provides a method to analyze NMR chemical shifts based binary fingerprints that have implications for encoding several properties of a molecule besides the basic framework or scaffold to determine its propensity towards a particular bioactivity class.

BACKGROUND AND PRIOR ART OF THE INVENTION

Traditionally structure elucidation of a given organic compound, either synthesized or naturally occurring is assisted by NMR mainly 1H and 13Cspectroscopy. First step in a spectral analysis is to detect the characteristic structural fragments and their corresponding chemical shift values. Chemical shift provides NMR its diagnostic power to routinely reveal conformation and stereochemistry at the functional group level. It is indicative of the overall structure of a molecule and explains its exact electronic environment as well as its local geometry and hybridization thus encoding several properties of the molecule including protein binding. Chemical shifts also enable identification of the environment of a proton and reveal the steric, electronic and spatial arrangement of the neighboring atoms. The factors affecting chemical shift values include electron density around proton, electronegativity of neighboring groups, anisotropic induced magnetic fields. It is represented by $\delta$ (delta) and is usually mentioned as part per million, (ppm). FIGS. 15 and 16 depict the typical chemical shift values (in ppm) of proton and carbon NMR of the commonly known fragment space. A molecule can be theoretically disintegrated into its constituent fragments wherein each of the fragments corresponds to a peak in the entire NMR spectrum with fixed chemical shift values on the ppm scale. An illustration is shown in FIG. 1 where both carbon and proton NMR of an organic compound 1 and the corresponding peak assignments of its constituent fragments are highlighted.

Fragment based virtual screening methods are gaining precedence in Lead Identification (LI) and Lead Optimization (LO) phases of drug discovery processes. Virtual drug like molecules can be generated combinatorially from a fixed number of possible chemical structural fragments therefore pre-screening fragments for their goodness of fit instead of fully enumerated libraries seems a more efficient approach. Although fragments sample most of the relevant chemical space yet they leave scope for ligand optimization in terms of hydrophilicity, hydrophobicity, steric features etc. to enhance their drug-likeness. The fragment libraries are characterized by biophysical analytical techniques like IR (Infra Red), NMR and Mass Spectroscopy. Because of its sensitivity and capability to capture details of neighboring environment of an atom NMR spectroscopy is the frequently used technique for identifying fragments that bind to a target protein.

Apart from structural elucidation, NMR also finds extended application in functional characterization of fragments in a molecule when present in a biological system. Group specific enzymes act on molecules possessing specific functional groups. For instance hydrolases act on amide, peptide, ester groups, lyases on double bonds, carbon-oxygen (C—O), carbon-sulfur (C—S) bonds, demethylases on methyl groups etc. Each fragment component in a compound makes some contribution to the overall biological activity. NMR based methods have been exploited in the field of drug design and discovery in the past. SAR by NMR is a prevalent technique in drug discovery to understand ligand interactions with target using chemical shift mapping to screen low binding ligands. The known experimental techniques in NMR based high throughput screening are reporting screening, spin labels, 3-FABS (Three Fluorine Atoms for Biochemical Screening), LOGSY (Ligand Observation with Gradient Spectroscopy), affinity tags etc. The techniques are not restricted to soluble proteins but are also available for membrane proteins which are equally attractive pharmaceutical targets. There are excellent reviews devoted to their description complete with successful case studies. The limitations arise when the protein has a big size or it forms large multimers or there is a large solvent exposed binding site In addition to that the high cost of equipment, maintenance along with requirement of high concentration of samples required to detect weak binding makes fragment based identification a challenging task. Therefore an in-silico approach to screen molecular fragments would be a preferred option.

There are a number of 'fragment based similarity' searching methods available in literature to rank molecules in a database. Computationally it is carried out by using binary dataset which encode presence or absence of certain substructure fragments in a given query molecule and compare with similar such features in the database entries. For high speed screening structural keys are generally represented as Boolean arrays and bitmaps where each bit represents an absence or presence of a structural feature. The known literature fingerprints viz. MDL MACCS 166-bit keys, circular fingerprints, ECFP, FCF2, Unity have been applied to a wide range of applications including prediction of absorption, distribution, metabolism, excretion and toxicity properties.

Conventional fragment based descriptors capture information without considering neighboring functional group environment and are insensitive to the total environment of a molecule. The similarity coefficients typically yield high similarity values when the reference molecule has just a few bits set in its fingerprint. To overcome these shortcomings some researchers have suggested the use of multiple similarity coefficients for example, Tanimoto, Cosine, Hamming, Russell Rao etc. but it was found that there is no single combination which works best for each and every activity class. In an earlier work Jurs in Anal Chem, 1988, 60, 2700-2706. has reported Carbon-13 magnetic resonance spectra simulation of various classes of small compounds. It was noted that chemical shift values encode several descriptors like presence of primary, secondary and tertiary carbons in the molecule, axial and equatorial bonds in cyclic systems and other topological features.

Article titled "New approaches for NMR screening in drug discovery" in Drug Discovery Today: Technologies Vol. 1, No. 3 2004 Ce'sar Ferna'ndez et al. discloses NMR screening techniques applied to drug discovery.

Article titled "Electron density fingerprints (EDprints): virtual screening using assembled information of electron density" by Albert J Kooistra et al. in *Journal of Chemical Information and Modeling* (*Impact Factor:* 4.3). December 2010; 50(10):1772-80 discloses a method to encode properties related to the electron densities of molecules (calculated (1)H and (13)C NMR shifts and atomic partial charges) in molecular fingerprints (EDprints.

Article titled "New approaches for NMR screening in drug discovery" in Drug Discovery Today: Technologies Vol. 1, No. 3 2004 Ce'sar Ferna'rndez et al. discloses NMR screening techniques applied to drug discovery.

Article titled "Electron density fingerprints (EDprints): virtual screening using assembled information of electron density" by Albert J Kooistra et al. in *Journal of Chemical Information and Modeling* (*Impact Factor:* 4.3). December 2010; 50(10):1772-80 discloses a method to encode properties related to the electron densities of molecules (calculated (1)H and (13)C NMR shifts and atomic partial charges) in molecular fingerprints (EDprints.

A cursory review of the prior art indicates that there is still a need in the art to provide an efficient method for high throughput screening in drug discovery. Therefore, the present inventors have come up with a novel method to compute and apply the NMR chemical shift based binary fingerprints for high throughput screening in drug discovery.

OBJECTS OF THE INVENTION

Main object of the present invention is to provide a method to compute and apply the NMR chemical shift based binary fingerprints for high throughput screening in drug discovery.

SUMMARY OF THE INVENTION

Accordingly, present invention provides a method to identify/analyze NMR chemical shift based binary fingerprints for virtual high throughput screening in drug discovery comprising:
i. subjecting an in silky designed molecule to verification for bad contacts, correct valency, charge, hybridization etc;
ii. estimating the both carbon and proton chemical shifts by adding the hydrogens and computing the frequency of occurrence of peaks in ppm to assign multiplicity in the fingerprints to quantify the chemical shifts and number of atoms;
iii. generating binary fingerprints of bit length of 1024 to accommodate the entire region of well-known proton and carbon chemical shift values to sufficiently capture the functional group variation in molecule which gets reflected in computed binary fingerprints;
iv. assigning each ppm block in the fingerprint 4 bits depending upon the number of peaks (H/C) corresponding to the intensity of the spectrum in that region; and
v. generating the cumulative spectra followed by calculating the similarity score to determine class specific fingerprints.

In an embodiment of the present invention, the method may be optionally be coupled with other diagnostic tools useful for virtual screening.

In another embodiment of the present invention, the method converts the experimental/predicted chemical shifts into corresponding fingerprints based on ppm values that capture the electronic/chemical/steric environment of carbon/hydrogen (C, H) atoms along with number of atoms.

In yet another embodiment of the present invention, the method has implications for encoding several properties of a molecule besides the basic framework or scaffold to determine its propensity towards a particular bioactivity class.

In yet another embodiment of the present invention, the method provides a consensus NMR binary fingerprints approach to distinguish between molecules belonging to various activity classes.

In yet another embodiment of the present invention, the method uses the structural similarity which reflects in spectral similarity to differentiate between therapeutic classes of compounds.

In yet another embodiment of the present invention, the chemical shift based binary fingerprints are more effective in capturing the detailed fundamental level structural information to determine the diversity among a given set of molecules.

In yet another embodiment of the present invention, the method can detect correlation between all the compounds belonging to a particular therapeutic classes viz. antifungal, antiviral etc.

In yet another embodiment of the present invention, the presence of certain heteroatoms in the molecule leads to variation of chemical shift which can be monitored to detect the required functional groups which impart drug-likeness and target affinity to a ligand.

In yet another embodiment of the present invention, the method may be used as smart templates for focused combinatorial library design and can also be extended to multi-target drugs by including fragments with appropriate structural and chemical features capable of binding to many proteins.

In yet another embodiment of the present invention, the method theoretically creates 1024×2 (proton and carbon NMR) equal to 2048 descriptors for every molecule using chemical shifts fingerprints data.

BRIEF DESCRIPTION OF THE FIGURES

FIG. 1(*a*) depicts the Proton NMR peaks assignment of the corresponding constituent fragments of the spiro-cyclic compound 1 and FIG. 1(*b*) depicts the carbon NMR peaks assignment of the corresponding constituent fragments of the spiro-cyclic compound 1.

FIG. 2*c* depicts Comparison of Tanimoto coefficients of compounds 2 and 3 its symmetrical analogue using conventional and present approaches respectively FIG. 3 depicts PCA analysis of compounds from nmr-shiftdb2 and in house archive showing chemical diversity. The first and second components are plotted.

FIG. 12a depicts Similarity scores for randomly selected antibacterial compounds.

FIG. 12b depicts Selected anti-fungal compounds with highest and lowest similarity scores.

FIG. 14 depicts AUC graph for anti-bacterial and anti-fungal class of compounds obtained by using fingerprints (1024 bits) in LibSVM binary classifier.

FIG. 15 depicts Typical proton chemical shift δ of commonly occurring functional groups.

FIG. 16 depicts Typical Carbon-13 chemical shift δ of commonly occurring functional groups Results FIGS. 17A-B depict results for antibacterial dataset using SVM classifier.

DETAIL DESCRIPTION OF THE INVENTION

The present invention discloses a method to generate and analyze NMR chemical shift based binary fingerprints that has implications for encoding several properties of a molecule besides the basic framework or scaffold to determine its propensity towards a particular bioactivity class.

Figure 2A:
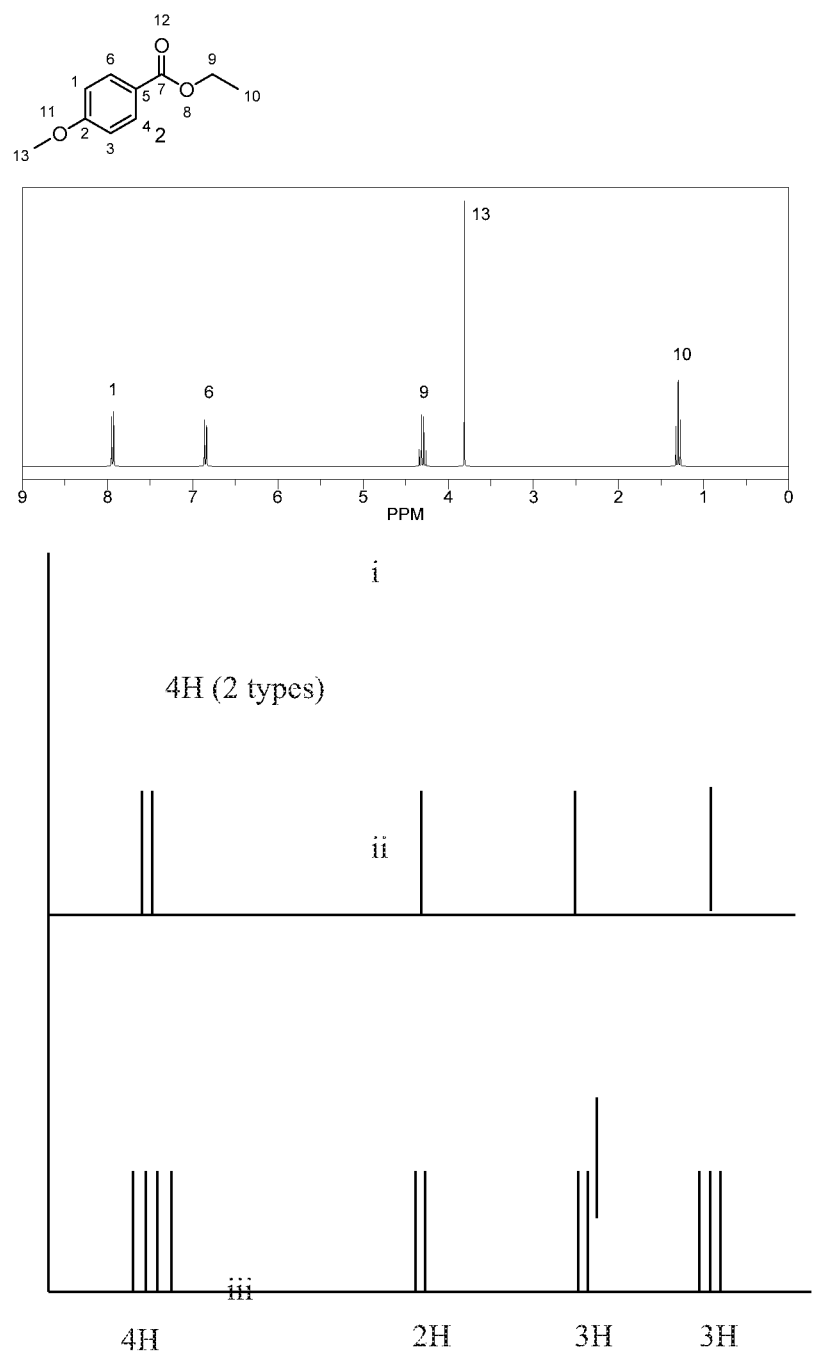
FIG. 2*a* depicts Proton-NMR spectrum of compound ethyl 4 methoxy benzoate 2(i), predicted spectra using conventional similarity search fingerprints (ii) and chemical shift based binary fingerprints (iii) Please note hydrogens are codified as bits.
Figure 2B:
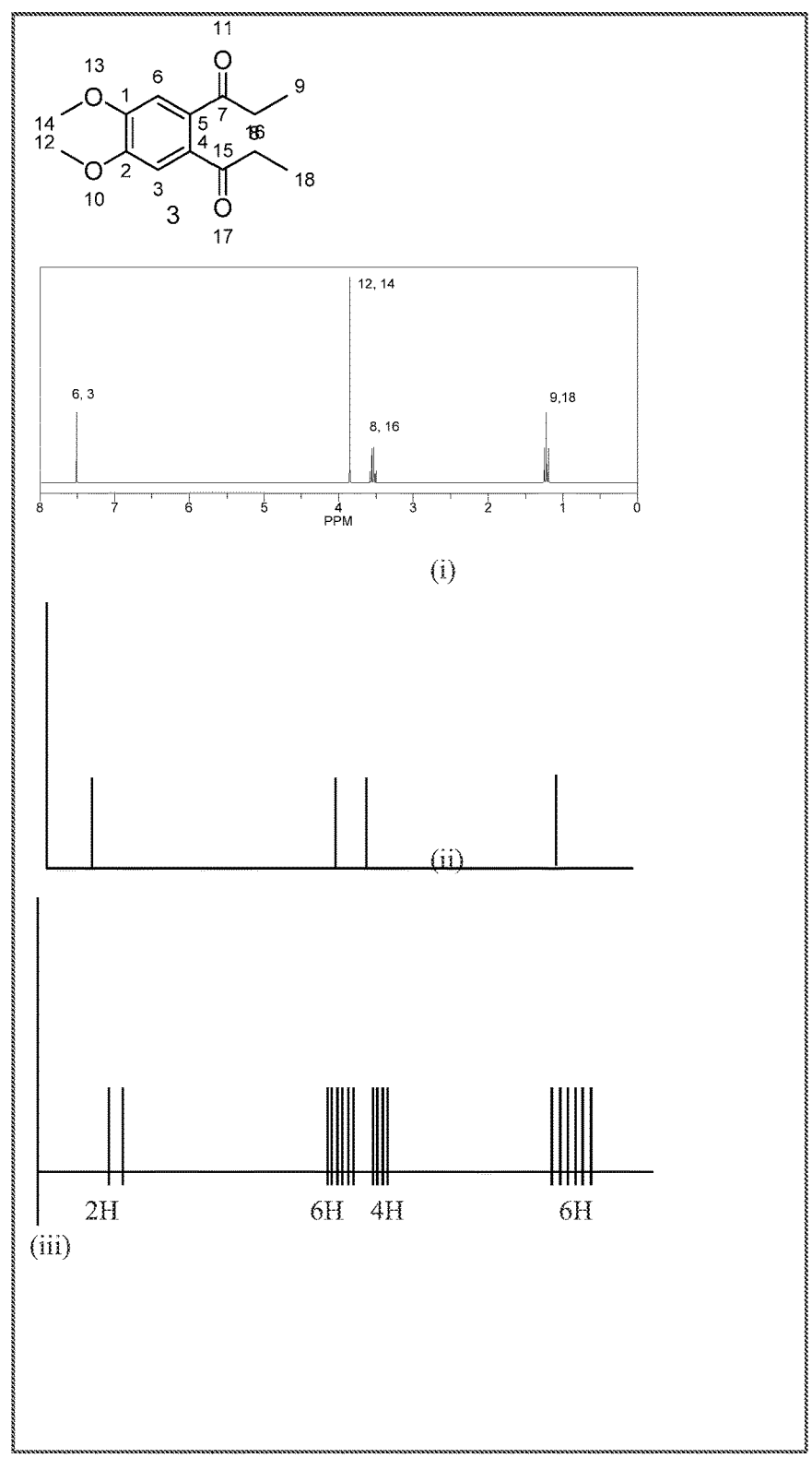
FIG. 2*b* depicts Spectral analysis of 1,1'-dimethoxy-1, 2-phenylene) bis (propan-1-one) 3, (i) predicted NMR spectra (ii) conventional similarity search fingerprints (iii) binary chemical shift based fingerprints where each hydrogen corresponds to one bit.

In an aspect, the invention provides a consensus NMR binary fingerprints approach to distinguish between molecules belonging to various activity classes. In this method, the inventors have converted the experimental/predicted chemical shifts into corresponding fingerprints based on ppm values that capture the electronic/chemical/steric environment of carbon/hydrogen (C, H) atoms along with number of atoms. For example the experimentally obtained spectrum of ethyl 4-methoxy benzoate molecule 2 shows five major peaks which if converted into conventional fingerprints of a search algorithm will occupy five bits. FIG. 2m. In the present method, one atom (proton) is represented by a single bit, so four protons are represented by four bits in the aromatic region of the fingerprint of compound (2). This increases the density of bits to be allocated in a NMR binary fingerprint, 12 bits in this case and 18 bits for its symmetrical analogue 1-(4, 5-dimethoxy-2-propanoylphenyl)propan-1-one (3) which has only four peaks in its experimental spectrum. The similarity coefficient for 2 and 3 will give a Tc value (Tanimoto coefficient) of 1.0 using conventional fingerprints whereas the NMR fingerprint based approach will yield a Tc value of 0.5 in a hypothetical similarity searching experiment. FIG. 2c. Thus the chemical shift based binary fingerprints are more effective compared to the conventional fingerprints in capturing the detailed fundamental level structural information to determine the diversity among a given set of molecules.

The present work is based on the hypothesis that structural similarity is reflected in spectral similarity which can be used to differentiate between therapeutic class of compounds. It is an analytical experiment based technique which can detect correlation between all the compounds belonging to particular therapeutic classes viz. antifungal, antiviral etc. Using these methodology structural regions common among biologically active classes of compounds based on computed ppm values which are comparable to experimental data can be identified. The presence of certain heteroatoms in the molecule leads to variation of chemical shift which can be monitored to detect required functional groups which impart drug-likeness and target affinity to a ligand. The detected virtual regions in the molecules serve as guidelines to design a compound and decide what fragments should be incorporated in a lead molecule for a particular bioactivity class. These in turn can be used as smart templates for focused combinatorial library design. The approach can also be extended to multi-target drugs by including fragments with appropriate structural and chemical features capable of binding to many proteins. However care should be taken to avoid common multi-activity fragments having chemical moieties known to cause side effects in drugs. Refer M Karthikeyan, R Vyas Predictive Methods for Organic Spectral Data Simulation Practical Chemoinformatics, 375-414 (2014); M. Karthikeyan, Arvind Bhaysar, Renu Vyas, Chem-Screener: A distributed computing tool for scaffold based virtual screening. Journal of Combinatorial Chemistry and High Throughput Screening. In press (2014).

EXAMPLES

Following examples are given by way of illustration and therefore should not be construed to limit the scope of the invention.

Materials and Methods

Databases nmrshiftdb2 is a free database (web database) of NMR spectral data of organic structures including prediction of $^{13}C$, $^{1}H$ and other nuclei to facilitate spectra searching, structure searching, key word searching and condition data based searching. For this study we also included a large collection (~1,30,000) of experimentally determined peak values of NMR (1H and 13C) spectra.

Softwares

The well-established known qualitative chemical shift prediction studied for $^1$H and $^{13}$C are ChemDraw, ChemAxon, ACD, MestReNova, Gaussian, Nmrshiftdb2, Abbott Prediction program, CHARGE. The binary classification model was built using SVM Lib classifier implemented in Weka and Rapid mineiprograms. Operators used were SVM Lib learner with default parameters and X-Validation operator for cross validation.

EXAMPLE

Figure 4:
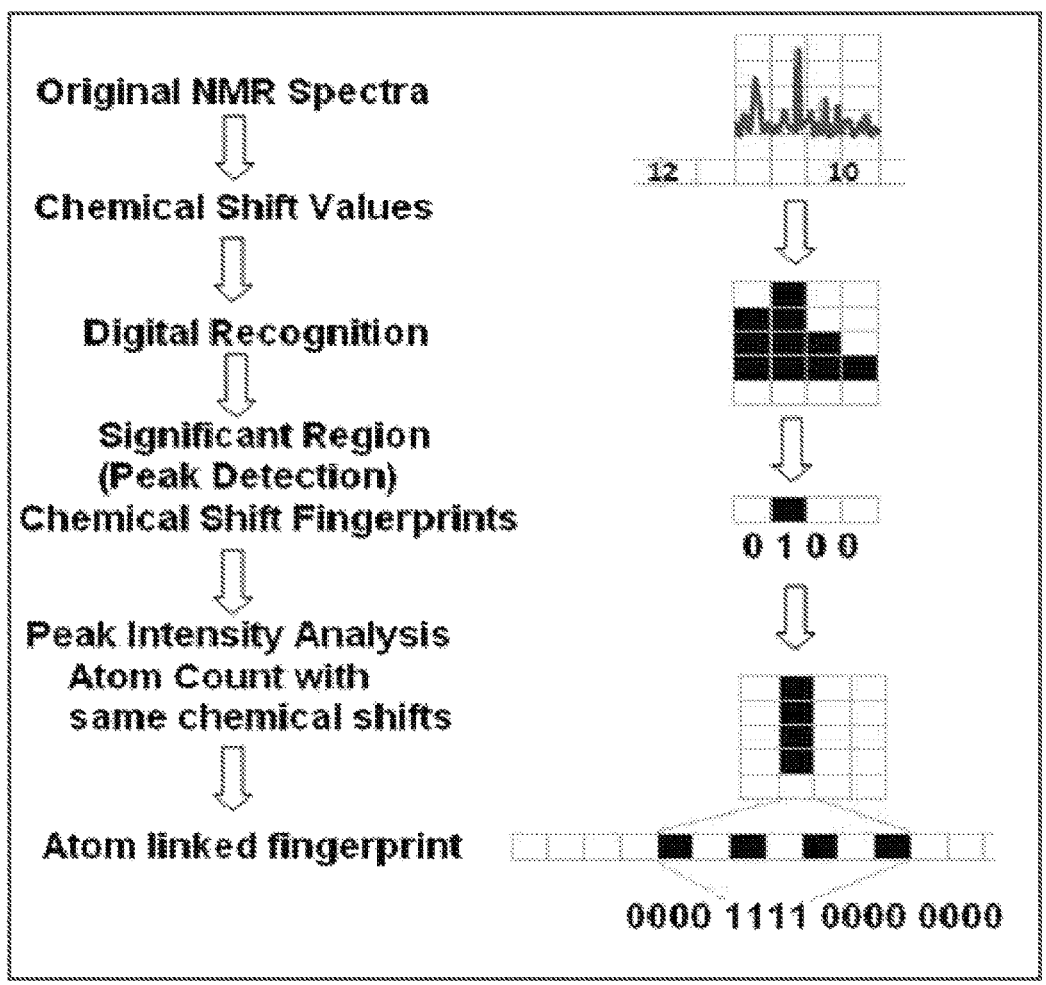
FIG. 4 depicts Workflow for conversion of experimental chemical shift into binary finger prints.

The inventors have carried out PCA analysis of about 40,000 organic compounds available in nmrshiftdb2 and an in house NMR data archive to ascertain the diversity of the starting molecule dataset used for computing binary fingerprints. As noted in FIG. 3 the first and second principal component scores based on 186 predicted 2D molecular descriptors that encompasses reasonable chemical space. From this dataset of original NMR spectra the inventors have used reported chemical shift values to generate the binary fingerprints. Conventionally, the area of the peak at specific positions represents the number of atoms with similar environment. In the instant approach if there is a peak in the region the bit is allocated to the highest peak, peak intensity analysis is performed via atom count with same chemical shifts (FIG. 4). Next, the inventors have statistically analyzed the bits based on frequency of occurrence of particular peaks in NMR spectra.

Figure 5:
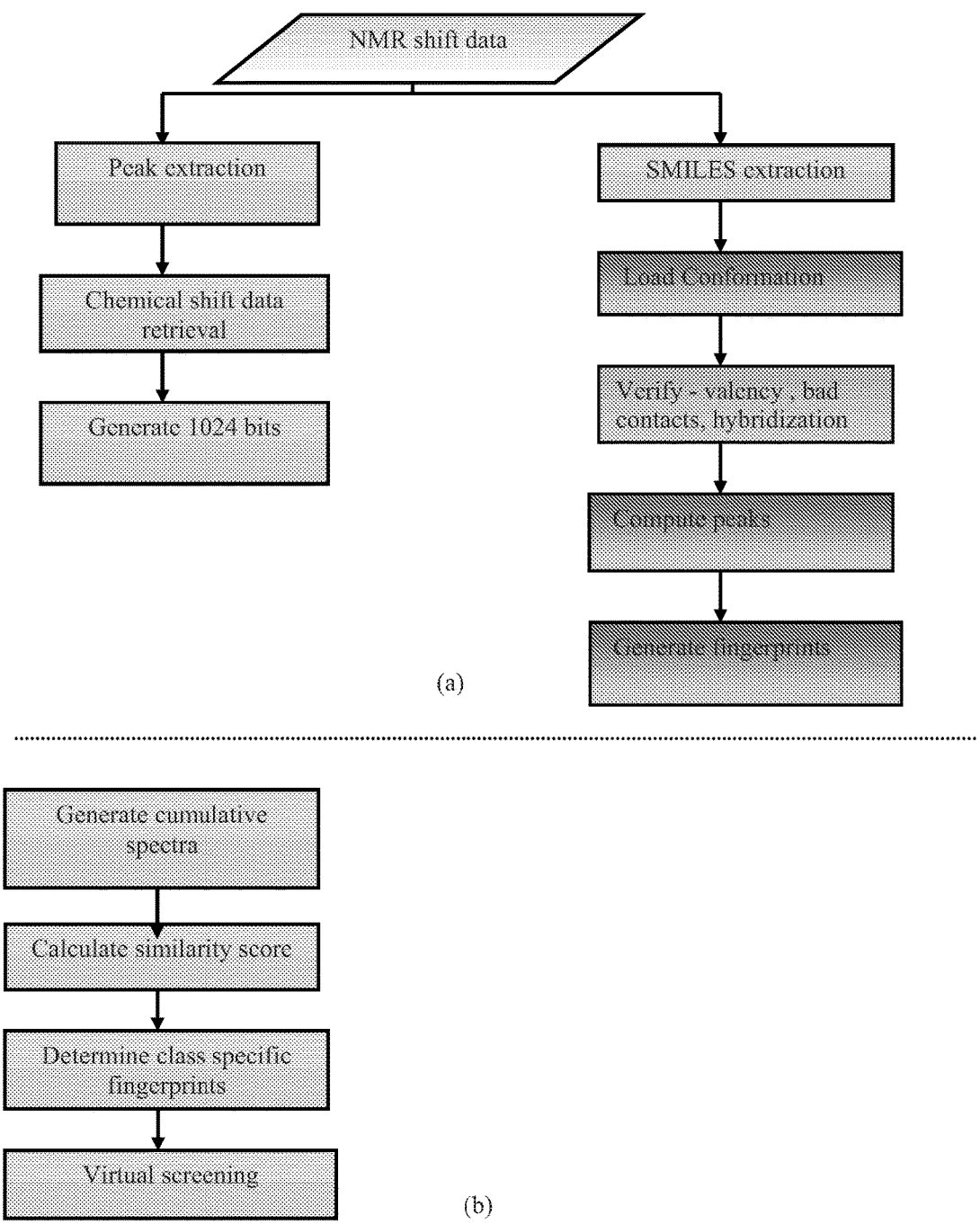
FIG. 5a depicts Computational steps in fingerprint generation algorithm 5b: NMR binary fingerprints based virtual screening workflow.
Figure 6:
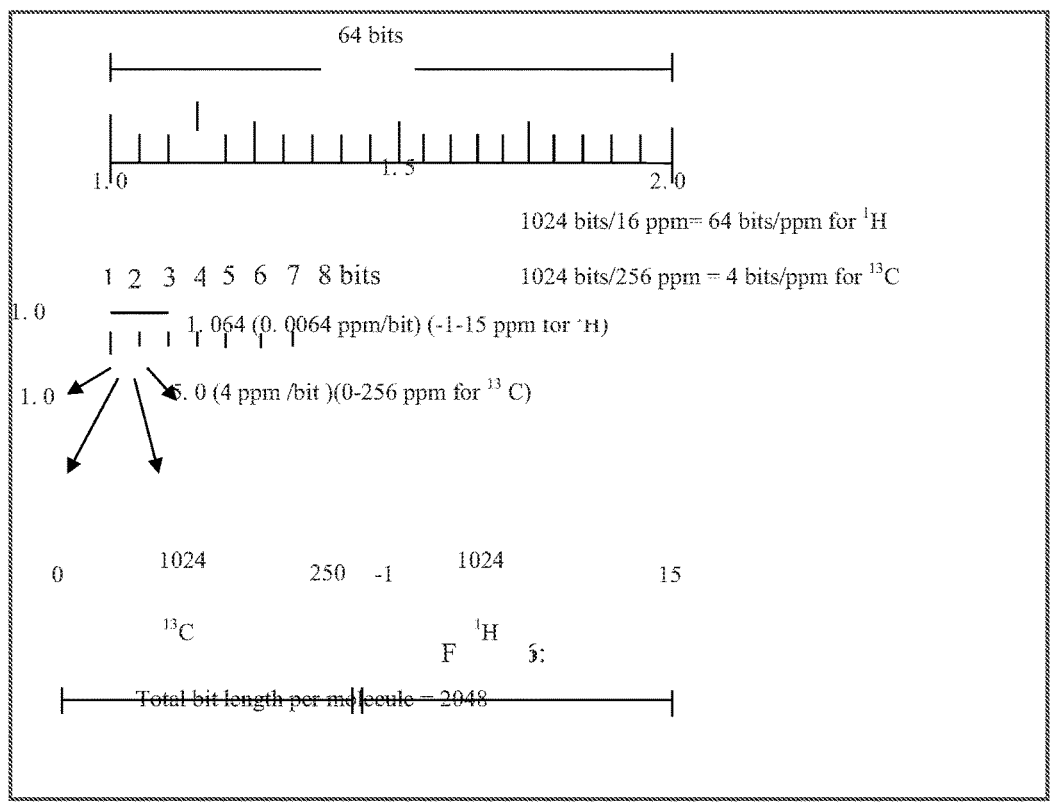
FIG. 6 depicts Allocation of bits in ppm block of a NMR spectrum in the instant method.

Detailed steps involved in implementation of the present software program are discussed below (FIGS. 5a and 5b). An in-silico designed molecule is first subjected to verification for had contacts, correct valency, charge, hybridization etc. The hydrogens are added and then both carbon and proton chemical shifts are estimated. The frequency of occurrence of ppm is computed to assign multiplicity in the fingerprints to quantify the chemical shifts and number of atoms. This is followed by generation of binary fingerprints of bit length 1024 to accommodate the entire region of well-known proton and carbon chemical shift values. Each ppm block in the fingerprint is assigned 4 bits depending upon the number of peaks (H/C) corresponding to the intensity of the spectrum in that region. For proton based fingerprints, the invention utilizes a chemical shift range of −1 to 15 ppm so that range for each bit is 16/1024=0.015, similarly for carbon a chemical shift range of 0-250 ppm so 251/1024=0.245 as depicted in FIG. 6. Thus every 0.01 ppm region in proton NMR and 2 ppm region in carbon NMR is characteristic of that particular class of compound and is sufficient to capture the variation in molecule which gets reflected in computed binary fingerprints and provides the diagnostic power to use this methodology for virtual screening. The present invention theoretically creates 1024×2 (proton and carbon NMR) equal to 2048 descriptors for every molecule using chemical shifts fingerprints data. In 1024 bits for every molecule it is desired to observe which bins are related to drug like and non-drug like attributes white ascertaining the peak regions corresponding to drug molecules. Depending on the complexity and chemical environment of molecules corresponding bits position of chemical shift will be occupied. The steps for virtual screening algorithm involve generation of cumulative spectra from the binary fingerprints of individual molecules in the dataset. A similarity score is obtained by identifying commonly occupied bits. The class specific discriminatory fingerprints are determined and used for virtual screening of a ligand library.

Figure 7A:
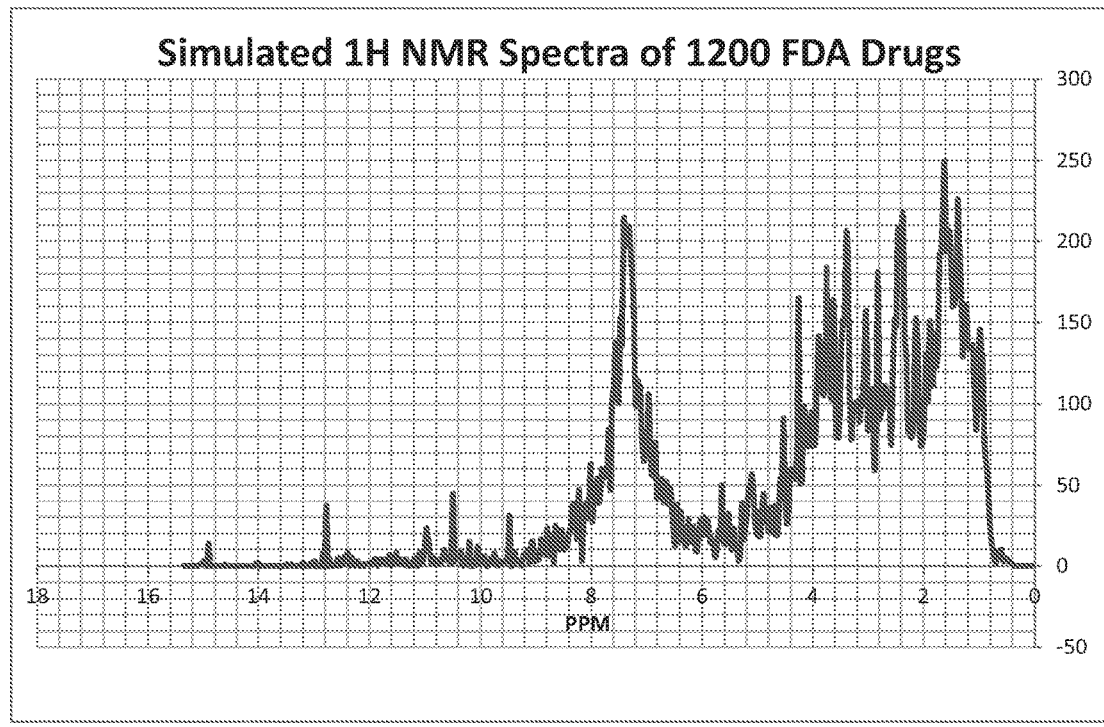
FIG. 7a depicts Cumulative proton spectra of 1200 drugs available in FDA database.
Figure 7B:
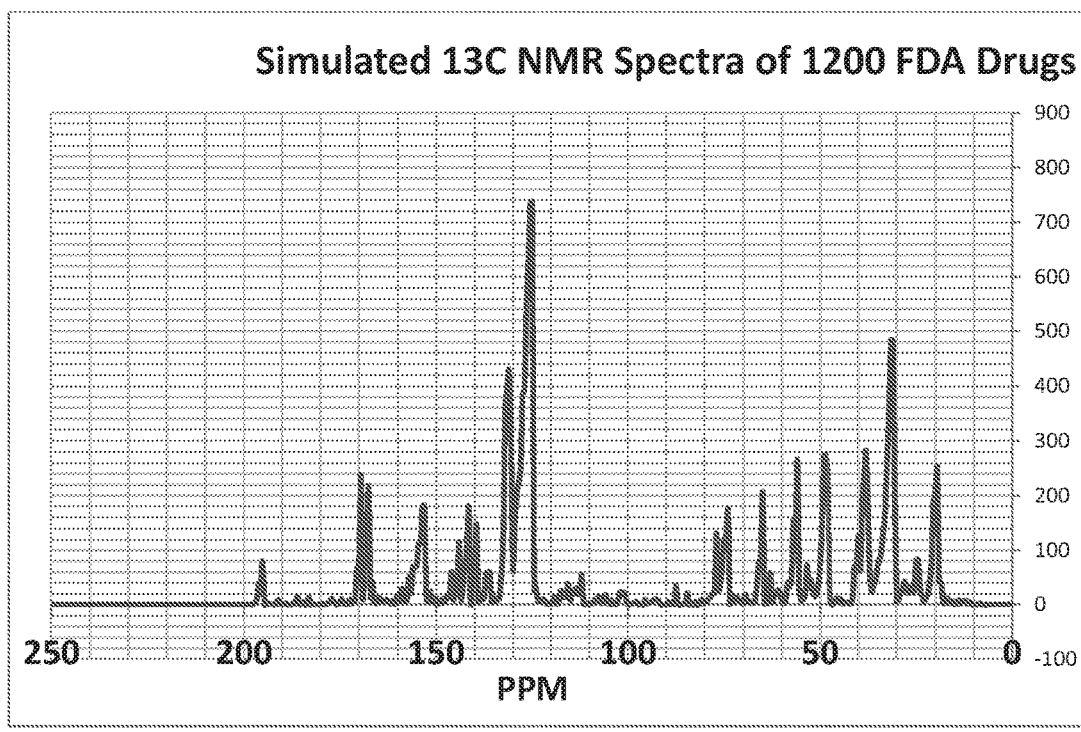
FIG. 7b depicts Cumulative Carbon-13 spectra of drug molecules in FDA database.

In the instant invention the entire drug space is mapped using chemical shift based fingerprints. In order to achieve this mapping the inventors have generated 'cumulative' NMR spectra of proton and carbon nuclei of 1200 compounds deposited in FDA database. (FIGS. 7a and b) Statistically significant regions of corresponding fingerprints of these reference spectra are used for virtual screening library of compounds. A molecule whose predicted NMR chemical shifts matches either with other molecules in the dataset or with the cumulative NMR model qualifies as a hit.

Figure 8A:
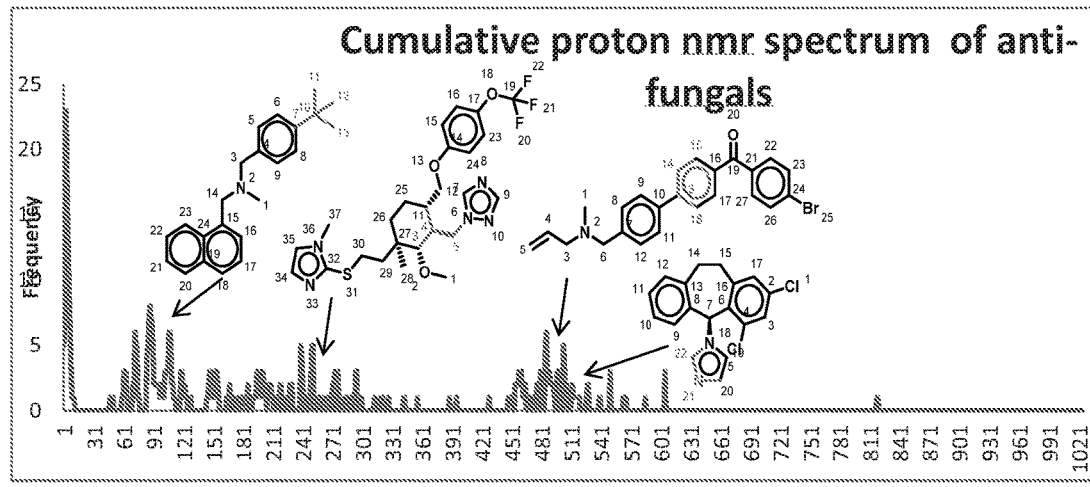
FIG. 8a depicts Cumulative NMR proton spectrum of antifungal compounds belonging to antiviral bioactivity class depicting the characteristic peaks and the corresponding major fragments identified.
Figure 8B:
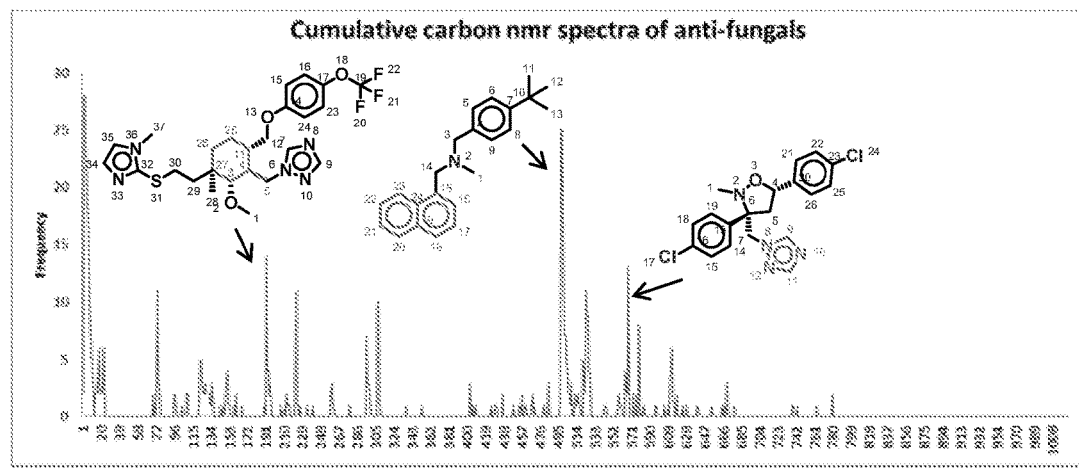
FIG. 8b depicts Cumulative carbon NMR spectrum of antifungals.
Figure 9A:
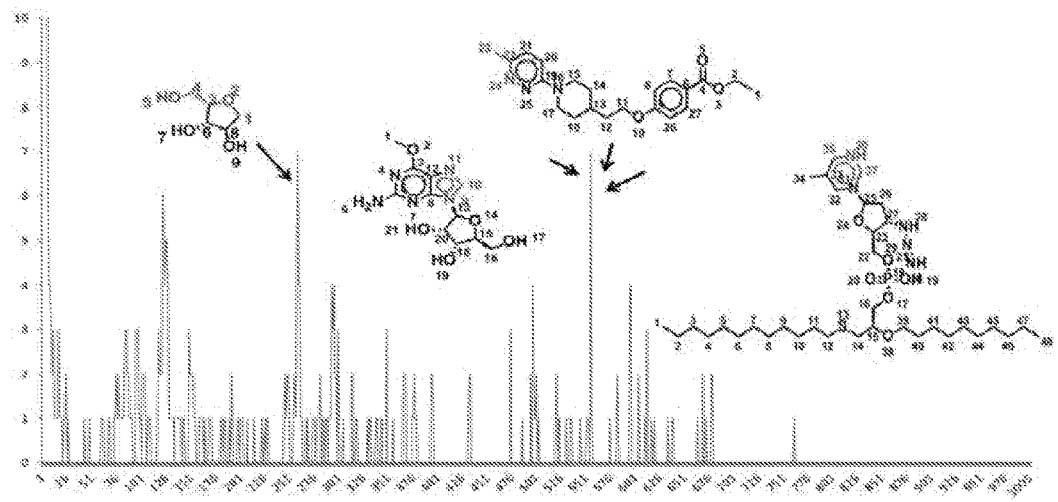
FIG. 9a depicts Cumulative carbon NMR of compounds belonging to antiviral bioactivity class depicting the most frequent peaks at bit positions corresponding to the major fragments present in class of molecules.
Figure 9B:
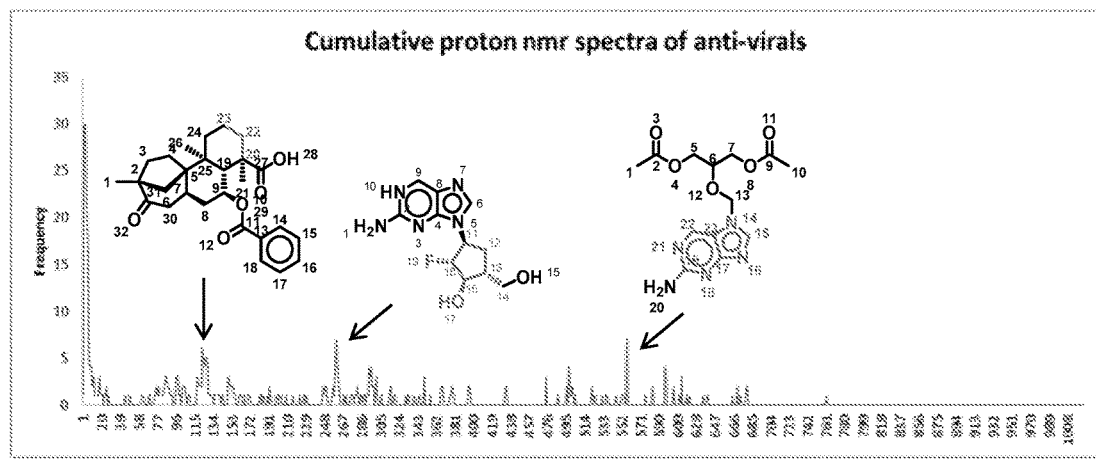
FIG. 9b depicts Cumulative proton NMR of compounds belonging to antiviral bioactivity class depicting the characteristic peaks and the corresponding fragments identified.
Figure 10A:
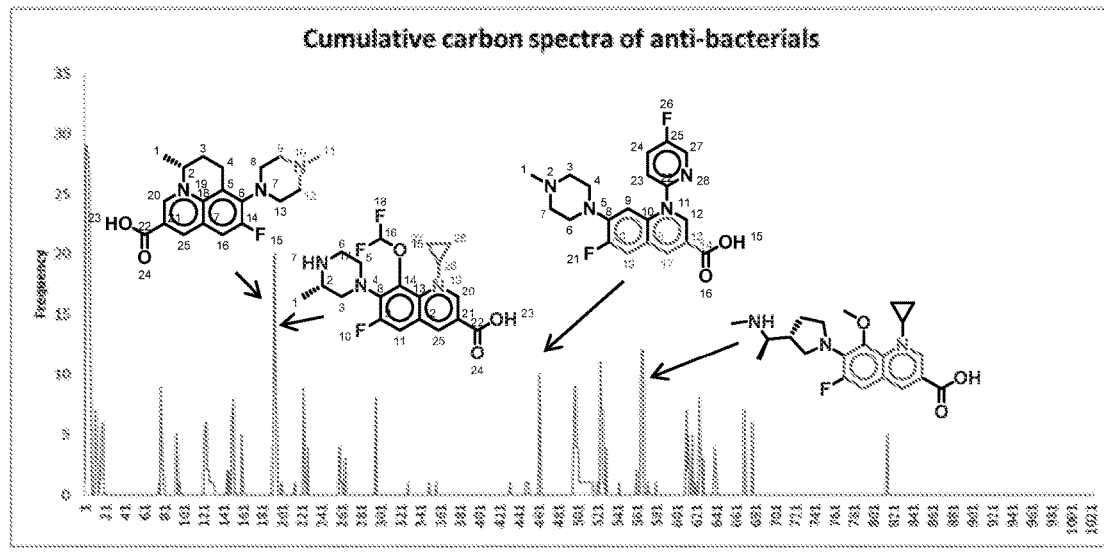
FIG. 10a depicts Cumulative carbon NMR of compounds of anti-bacterial class depicting the characteristic peaks corresponding to frequently occurring fragments at characteristic bit positions obtained from peaks ppm to bit value conversion tables.
Figure 10B:
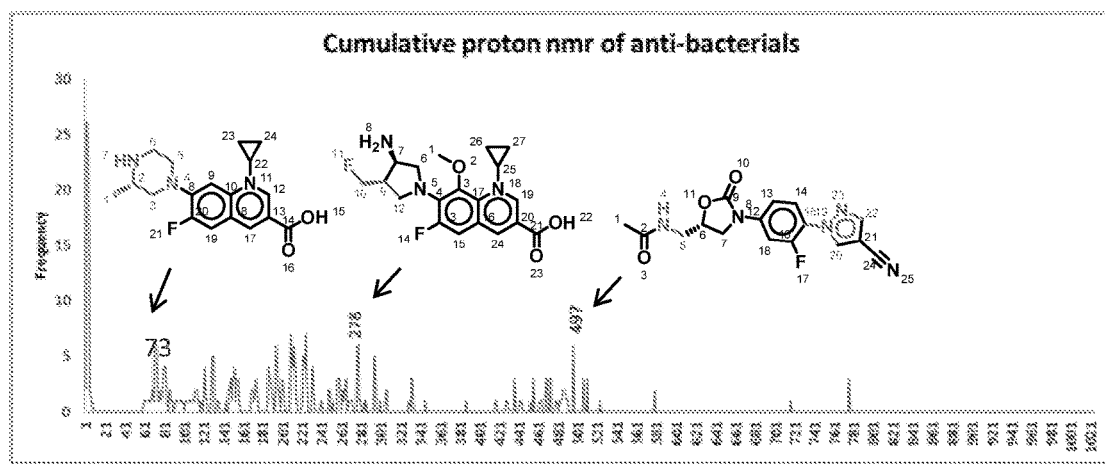
FIG. 10b depicts Cumulative proton NMR of compounds belonging to anti-bacterials bioactivity class depicting the characteristic peaks at bit positions corresponding to the frequent fragments.

In order to validate the effectiveness of the chemical shift fingerprint based approach the inventors have used a set of therapeutically important compounds from each of the following classes anti-bacterial (AB), anti-fungal (AF) and anti-virals (AV) classes extracted from literature. These compounds are subjected to prediction studies to identify the NMR fingerprint regions and their chemical class which are very specific to their corresponding therapeutic category. Cumulative spectra of individual bioactive classes with some selected representative fragments are shown in FIGS. 8-10. The X axis shows the number of bits allocated (1024) and the frequency of the most commonly observed fragments for that class of compounds is plotted on the Y axis. The 'peak ppm values to bit position' for carbon and hydrogen spectra of all compounds are given in FIGS. 15 and 16 below. The inventors have analyzed the molecules and their fragments which correspond to the most frequent bits in the cumulative proton and carbon spectra.

Figure 11:
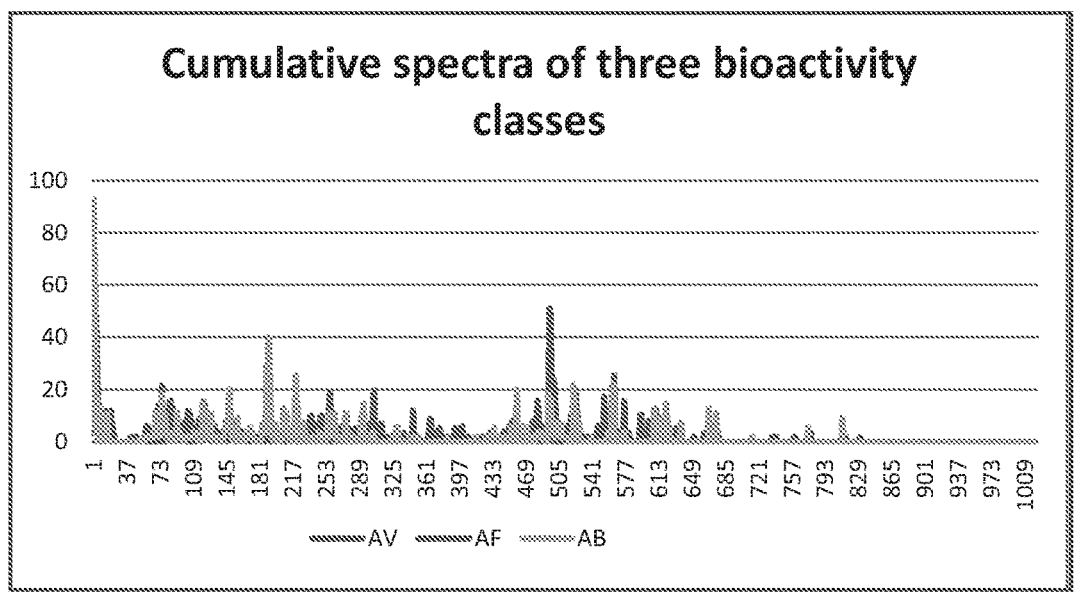
FIG. 11 depicts Derived cumulative spectrum showing distinct peaks characteristics of four drug classes—antifungal (AF), antibacterial (AB) and antiviral (AV) class of compounds.

The cumulative proton and carbon spectra of antifungal class of compounds are explained as a representative example. Anti-fungals show a propensity towards chiral napthyl substituted core containing compounds (FIG. 8). The four representative molecules highlighted are the ones having the maximum bit occupancy for certain preferred fragments. In the first molecule depicted in the proton spectrum of anti-fungals, the bit position value 87 converted to 1.375 ppm (on NMR scale) having a frequency value of 8 corresponds to the tertiary butyl methyl group fragment in that molecule. Similarly the second important peak with bit value 240 (3.75 ppm) and frequency 5 corresponds to the fragment containing methyl protons at 5 position flanked by cyclohexyl and triazolyl rings in the second molecule, third peak at bit position 486 (7.625 ppm) with a frequency 3 corresponds to aromatic protons numbered 14 and 18 in third molecule and the fourth peak at bit position 503 (7.875 ppm) and frequency 5 denotes presence of an imidazole ring fragment in fourth molecule. Cumulative carbon NMR spectra of antifungals complemented the fragment information collected from proton NMR. The three major peaks at bit positions 192, 498 and 568 are studied and representative compounds having fragments corresponding to them are depicted in FIG. 8b. The bit position at 192 corresponds to 48 ppm on the carbon NMR scale encodes for the methyl carbon attached to oxygen, bit position 498 corresponding to 125 ppm in carbon NMR encodes for the napthyl region in second representative compound and bit position at 568 (142 ppm) possesses the fragment with a triazole ring system. Likewise fragments corresponding to molecular peaks in the cumulative spectra of the remaining two bioactive classes are also subjected to in depth analysis. Anti-virals preferred substituted pyrimidines, oxazolines and furan ring fragments containing structures while the anti-bacterials spectrum is dominated by long chain piperidine containing fragments. (FIGS. 9-10) A combined 'cumulative' spectra of the three drug classes studied is generated to identify the discriminatory distinct NMR peaks (after eliminating the noise)

belonging to individual class. (FIG. 11) These distinguishing peaks encode non-redundant fragments discriminatory for that activity.

Figure 12C:
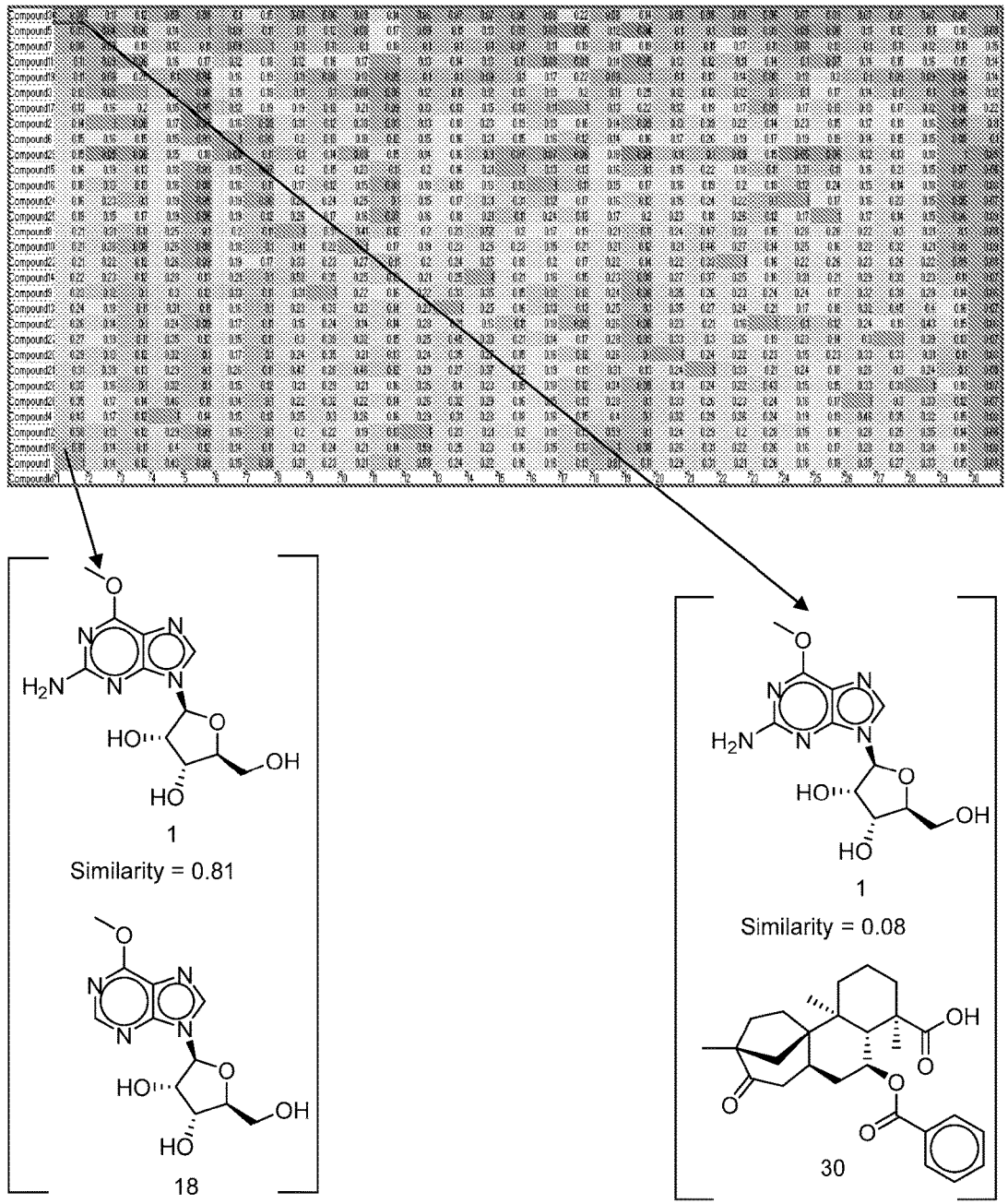
FIG. 12c depicts Similarity score obtained for randomly selected anti-viral compounds.
Figure 13:
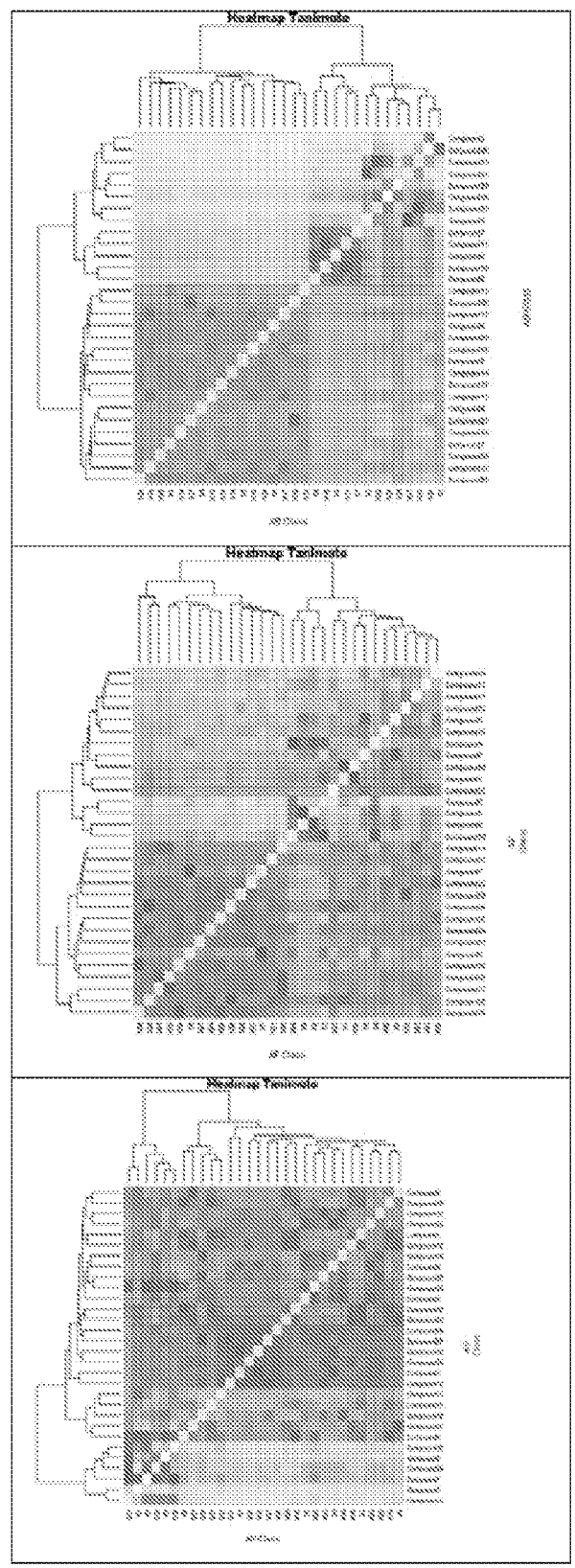
FIG. 13 depicts Heat maps for all the three drug classes (AB, AV, and AP) showing different profiles.

The invention demonstrates the practical use of the binary fingerprints (1024 bits) of carbon and proton in virtual screening. For this, Tanimoto coefficient score, C—H NMR spectra similarity score, $^{13}$C-NMR spectra similarity score and $^{1}$HNMR spectra similarity score matrices are generated for molecules of all activity classes. From the C—H NMR spectra matrix generated for each class, structure of the molecules representing the highest and the lowest similarity scores are specifically probed. The results show compounds having high similarity score to be structurally similar with a difference of one or two functional groups and conversely compounds with low similarity scores are found to be structurally diverse. For example compounds 6 and 28 among anti-bacterials give a similarity score of 0.80 and possess similar structures whereas compounds 1 and 30 among anti-virals display a low similarity score of 0.08 and are structurally quite diverse. (FIGS. 12a and b) Likewise anti-fungal compounds 7 and 8 having similar structures except for the substitution of a triazole moiety by a morpholine ring at position 4 of the central cyclohexyl ring in the latter, give a similarity score of 0.88 and completely diverse compounds 14 and 27 give a score of 0 or null. (FIG. 12c) A heat map is generated using Tanimoto similarity coefficient for all the drug classes and as expected differences are noted in the heat map profile of all molecules belonging to the three activity classes (FIG. 13).

In order to further validate the method, fingerprints data of molecules (1024×2 descriptors) from two classes viz. anti-fungal and anti-bacterial were given as input into Support Vector Machine (SVM) a binary classifier for quantitatively observing the selectivities of these fingerprints in detecting the bioactivity class. The machine learning results shown accuracy of 83.7%, class precision for antifungal compounds is 80.8% and 88.46% for anti-bacterials and recall values are 90.4% and 76.6% respectively as shown in FIG. 17A. The AUC value obtained is 0.89 thus indicating the NMR model to be statistically valid for practical applications (FIG. 14)

ADVANTAGES OF THE APPLICATION

The present invention has three important applications of the proposed methodology. The first one is similarity searching viz. spectra comparison using NMR based fingerprints, if the fingerprints are found to be possessing 90% or more similarity then those compounds can be assumed to be similar. Another potential application is to generate spectra for compounds not yet synthesized in the laboratory. Chemical shifts could be predicted for other nuclei such as silicon $Si^{29}$ and selenium $Se^{77}$ containing compounds whose spectra are difficult to obtain experimentally. Third application relates to fragment based characterization of a class of molecules by identifying the set of fragments, linkers, functional groups, scaffolds and design of a virtual library. The library can be further screened for the presence of drug like and lead like compounds.

Thus the present invention provides a new method for virtual high throughput screening in drug discovery based on chemical shift based binary fingerprints. The present methodology tries to simulate/mimic analytical data used for structural elucidation of compounds including the stereochemical, conformational and electronic environment of atoms which play a significant role in determining bioactivity. The cumulative proton and carbon spectra of FDA molecules serve as a ready reference to screen drug and non-drug like compounds. For the present study chemical shift data value ranges for proton (−1 to 15 ppm) and carbon (0-200 ppm) NMR spectroscopy of organic molecules is employed to compute binary fingerprints. The NMR fingerprints characteristic of a drug class have been developed as smart filters for virtual screening of molecular databases. Drug like/lead like classification using SVM is performed on these datasets which gave an AUC of 0.89 demonstrating the effectiveness of this approach for virtual screening. The program can be deployed in a distributed computing environment to enable faster screening.

We claim:

1. A method to identify NMR chemical shift based binary fingerprints for virtual high throughput screening in drug discovery comprising:
    a) subjecting an in silico designed molecule to verification for bad contacts, correct valency, charge and for hybridization to provide a verified in silico designed molecule;
    b) adding hydrogens to the verified in silico designed molecule, computing frequency of occurrence of peaks in ppm to assign multiplicity in the fingerprints, and obtaining carbon chemical shifts, proton chemical shifts and number of atoms;
    c) generating a computed binary fingerprints of a 1024 bit length to accommodate the entire region of known proton and carbon chemical shift values, wherein functional group variation in the in silico designed molecule is reflected in the computed binary fingerprints;
    d) assigning 4 bits to each ppm block in the computed binary fingerprint by using the number of peaks (hydrogen/carbon) and intensity of the spectrum in that region;
    e) generating cumulative spectra; and
    f) calculating the similarity score to determine class specific fingerprints.

2. The method according to claim 1, further comprising applying other diagnostic tools useful for virtual screening.

3. The method according to claim 1, wherein the method converts experimental or predicted chemical shifts into corresponding fingerprints based on ppm values that capture the electronic, chemical, and steric environment and number of carbon/hydrogen (C, H) atoms ms.

4. The method according to claim 1, wherein the method encodes properties of a molecule in addition to the basic framework or scaffold, wherein the properties determine propensity of the molecule towards a particular bioactivity class.

5. The method according to claim 1, wherein the method provides consensus NMR binary fingerprints that distinguish between molecules belonging to activity classes.

6. The method according to claim 1, wherein the similarity score differentiates between therapeutic classes of compounds.

7. The method according to claim 1, wherein the binary fingerprints capture detailed fundamental level structural information to determine the diversity among a given set of molecules.

8. The method according to claim 1, wherein the method detects correlation between all compounds belonging to a therapeutic class.

9. The method according to claim 1, wherein heteroatoms in the molecule vary the chemical shift which is monitored to detect the required functional groups which impart drug-likeness and target affinity to a ligand.

10. The method according to claim 1, wherein the method is used as a smart template for focused combinatorial library design and is extended to multi-target drugs by including fragments with appropriate structural and chemical features capable of binding to many proteins.

11. The method according to claim 1, wherein the method creates 2048 descriptors for every molecule using chemical shifts fingerprints data.

12. The method according to claim 8, wherein the therapeutic class is an antifungal or antiviral.

13. A method of determining the propensity of a molecule to have a particular bioactivity, comprising:
   a) subjecting an in silico designed molecule to verification for bad contacts, correct valency, charge and for hybridization to provide a verified in silico designed molecule;
   b) adding hydrogens to the verified in silico designed molecule, computing frequency of occurrence of peaks in ppm to assign multiplicity in the fingerprint, and obtaining carbon chemical shifts, proton chemical shifts and number of atoms;
   c) generating a computed binary fingerprint of a 1024 bit length to accommodate the entire region of known proton and carbon chemical shift values, wherein functional group variation in the molecule is reflected in the computed binary fingerprint;
   d) assigning 4 bits to each ppm block in the computed binary fingerprint by using the number of peaks (hydrogen/carbon) and intensity of the spectrum in that region;
   e) generating a cumulative spectrum;
   f) calculating the similarity score from the cumulative spectrum to determine a class comprising specific fingerprints; and
   g) comparing the similarity score to a similarity score of the molecule.

* * * * *